United States Patent

Vesterberg

[11] 4,054,490
[45] Oct. 18, 1977

[54] METHOD FOR INVESTIGATING MICROORGANISMS

[75] Inventor: Olof Alfred Yngve Vesterberg, Saltsjo-Duvnas, Sweden

[73] Assignee: Orion-Yhtyma Oy-Orion Diagnostica, Helsinki, Finland

[21] Appl. No.: 557,287

[22] Filed: Mar. 11, 1975

[30] Foreign Application Priority Data

Mar. 12, 1974 Sweden .................................. 7403259

[51] Int. Cl.² ............................ C12K 1/00; C12K 1/10
[52] U.S. Cl. ....................... 195/103.5 K; 195/103.5 R; 195/103.5 M; 195/127
[58] Field of Search ................. 195/103.5 R, 127, 139

[56] References Cited

U.S. PATENT DOCUMENTS

| 2,904,474 | 9/1959 | Förg | 195/103.5 R |
| 3,107,204 | 10/1963 | Brown et al. | 195/103.5 R |
| Re. 24,557 | 10/1958 | Scherr | 195/103.5 R |

Primary Examiner—Lionel M. Shapiro
Assistant Examiner—Robert J. Warden
Attorney, Agent, or Firm—Stevens, Davis, Miller & Mosher

[57] ABSTRACT

A method of investigating the effect of a biologically active agent, present in degrees of concentration increasing from one end to the other in an elongate carrier for the agent, said carrier being applied to microorganisms cultivated on an elongate continuous cultivating substance, the required concentration of the agent, for it to be effective, corresponding to the distance alongside said carrier over which growth of colonies of microorganisms is not visible.

7 Claims, 6 Drawing Figures

U.S. Patent   Oct. 18, 1977   Sheet 1 of 2   4,054,490
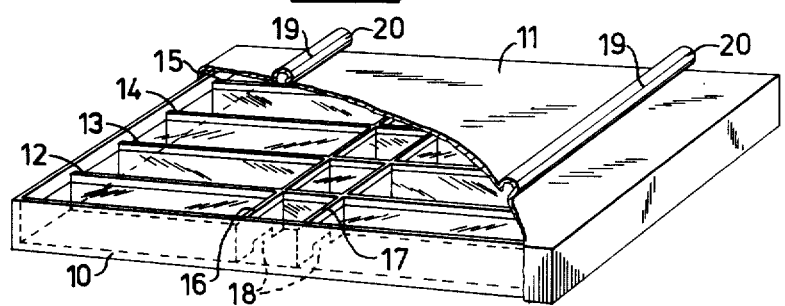
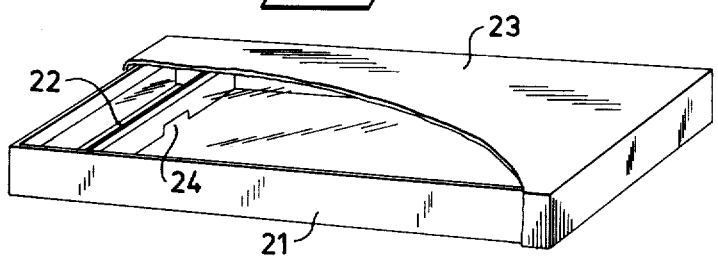
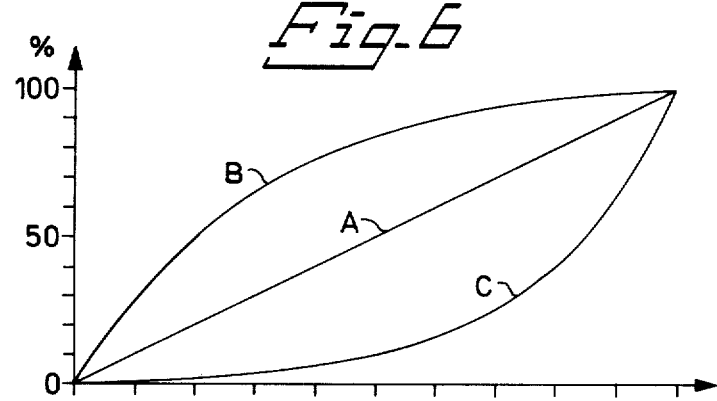

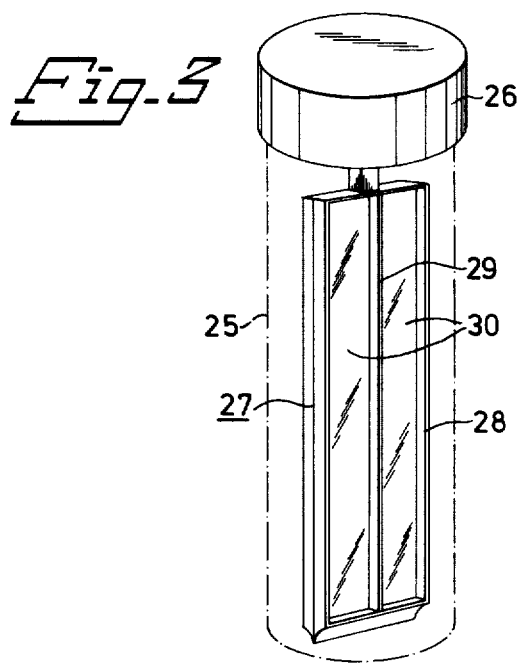
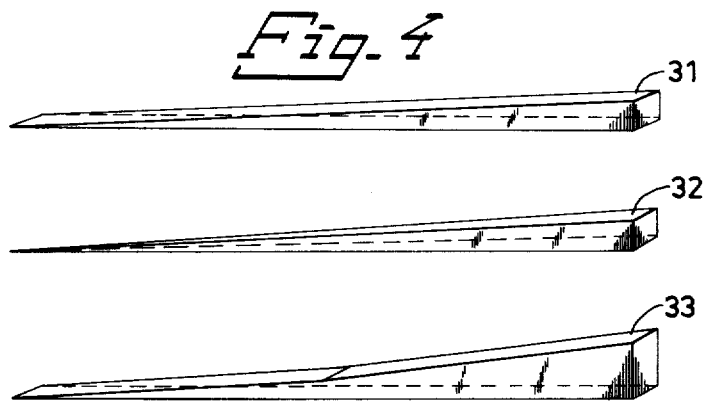
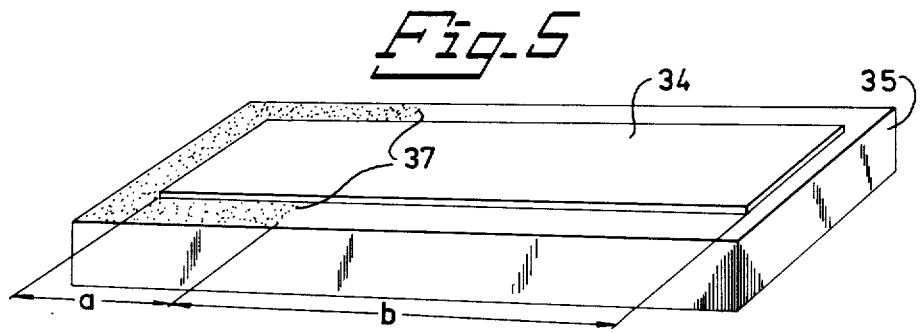

METHOD FOR INVESTIGATING MICROORGANISMS

The present invention relates to a method for the investigation of the effect of a biologically active substance on microorganisms, which are cultivated in the presence of a continuous cultivating substance. By "microorganisms" is here understood, apart from bacteria, rickettsia, viruses, bacteriophages, also such fungi as mold, yeast and slime fungi, and living cells. With "biologically active substances" is intended those which affect metabolism in a negative or positive way, for example promoting growth and/or multiplication of said microorganisms, such substances being vitamins, amino acids, nutrients and other growth factors and microorganisms having a stimulating effect on the first-mentioned microorganisms, also intended are those inhibiting growth and/or multiplication of, or killing said microorganisms, such as inhibitors, antibiotics, disinfecting agents and microorganisms having antagonistic effects on said first-mentioned microorganisms.

Within the medical and biological fields, especially in microbiology, there is often a need for investigations of the kind set forth in the introduction. As examples of such investigations can be mentioned isolation and classification of certain strains or mutants of microorganisms in mixtures of microorganisms, graduation of microorganisms with relation to how and to what degree they are affected in a positive or negative direction, or whether they are dependent on different biological active substances, and determining concentration of biologically active substances, such as determining the concentration of antibiotics in blood or urine samples for the health service and in foodstuffs in the foodstuff industry.

For investigations of the kind given above, discontinuous methods have been used previously to a certain extent, i.e. methods in which separate sample receptacles such as test tubes or Petri dishes have been used, with the biologically active substance varying in kind and/or concentration from receptacle to receptacle. Since it is often of interest to examine a large number of microorganisms, where there is the need to test each sample with many different concentrations or amounts of the biologically active substance in question, the discontinuous methods involve considerable effort and require large amounts of space, resulting in high costs and a considerable consumption of time.

For certain investigations of the aforementioned kind, the so-called "Paper Disc Procedures" have been used (described, amongst other places, in "American Journal of Clinical Pathology", 45 (1965) page 493). According to these, the microorganisms are cultivated in round Petri dishes in the presence of continuous cultivating substance, usually formed by a supporting substance consisting of agarel and nutrient consisting of a suitable nutritive medium. Small round discs of filter paper or tablets, which are saturated with antibiotics of different kinds of concentration, and having a diameter of about 0.5 cm are applied to the surface of the cultivating substance after inoculating it with the microorganisms. The antibiotic then diffuses out into the cultivating substance in a radial direction from the places of application, and the microorganisms multiply in number on the areas of the cultivating substance which have not obtained such a high concentration of antibiotic active against the microorganisms that said multiplication is inhibited. Nearest to the discs or tablets, where a relatively high concentration of antibotic is to be found, there is a zone where the presence of microorganisms is not visible, if the antibiotic is active against the microorganisms. The diameter or radius of this zone is measured and, if accurate standardizing measures have been taken, can be said to constitute a certain measure of the sensitivity of the microorganisms to the antibiotic in question. A relatively large difference in concentration, especially in the sections adjacent the points of application, is obtained between neighbouring points on each line directed radially in relation to the discs or tablets. This causes difficulties in perceiving different concentrations or effects thereof in said sections, resulting in low accuracy. The total measuring area is often limited to about 0.4 to 1.5 cm in a radial direction, which limits measuring possibilities. Furthermore, radial diffusion results in the concentration of antibiotics at each point near the places of application being altered rapidly with time during the critical period, i.e. during the first 8 hours. Into the bargain, the conditions are different for different kinds of antibiotics, amongst other things due to these often having different diffusion coefficients, and for different microorganisms, due to the latter having different rates of multiplication. This has an injurious effect on the precision ad repeatability of the disc methods, and even on their use in different fields. In summary, the methods based on radial diffusion are distinguished, whether the antibiotics or other biologically active substances are applied by round discs or tablets or are supplied in some other way, by the diffusion characteristics and degree of affinity to agar or other supporting substance of the different kinds of antibiotic or substance dictating the concentration pattern, which is furthermore subject to large and relatively rapid alterations with time, and by the distance being relatively small between the places with the lowest and highest concentrations, as well as the distance between positions, which have to be evaluated when reading-off, between these places.

The object of the present invention is to provide a new and advantageous procedure in investigations of the kind given in the introduction, which are not burdened with the aforementioned defects distinguishing the earlier methods of investigation.

With said object in view it is according to the invention suggested, in the investigation of the effect of a biologically active substance on microorganisms which are cultured in the presence of a continuous cultivating substance, to supply the biologically active substance to the cultivating substance along an elongated zone with an amount varying in a predetermined manner along the length of the zone. The biologically active substance will hereby diffuse out into the cultivating substance essentially solely transverse to the longitudinal direction of the supply zone, since the difference in concentration between neighbouring points in the plane running transverse to the longitudinal direction of the zone through the cultivating substance will be greater than the difference in concentration between neighbouring points in a plane parallel with the longitudinal direction of the zone through the cultivating substance. The biologically active substance will therefore distribute itself in the cultivating substance so that its concentration varies along the longitudinal direction of the supply zone in correspondence to the amount of biologically active substance which is supplied to each transverse section of the supply zone. It will thereby be possible to achieve in a simple manner nearly any desired concentration gradient in a previously determined direction in the cultivating substance, and the degree of effect by the biologically active substance on the microorganisms which are inoculated and cultivated on the cultivating substance can easily be read off by measuring the length of the supply zone, over which the multiplication of the microorganims is effected by the biologically active substance. Since the length of the supply zone and the variation along it of the amount of biologically active substance supplied to it can moreover be selected as desired, it will be appreciated that the concentration interval which, while using disc procedures for example, has been practically impossible to investigate satisfactorily, can be investigated with excellent accuracy and repeatability by utilizing the method according to the present invention.

The cultivating substance utilized as supporting substance in the method according to the invention is suitably the one customarily used in connection with corresponding investigations of microorganisms, and is for example agar or polyacrylamid gel or a solid porous material, for example paper or porous plastic. The supporting substance with its content of nutrient, i.e. nutritive medium for the microorganisms in question, in a way which is customary in connection with corresponding investigations of microorganisms, suitably allow the biologically active substance supplied to diffuse comparatively slowly out into it. In order to ensure that the distribution, by the method according to the invention, of the biologically active substance, in the cultivating substance will be retained during a considerable time, and also for facilitating matematical pre-calculation of this distribution it is suitable to use a cultivating substance in the shape of a body, having two definingg sides disposed on either side of the elongated supply zone and substantially parallel to it. It is thereby suitable that the distance between these two defining sides and the long sides of the supply zone and the thickness of the body are so small that the biologically active substance which is supplied has time to distribute itself essentially evenly over the cross section of the body, before the multiplication phase sets in for the microorganisms cultured in the presence of the cultivating substance, i.e. usually within 3–8 hours after cultivation starts.

The biologically active substance is suitably supplied to the cultivating substance and a carrier for the biologically active substance, said carrier having the ability of giving off to the cultivating substance along said zone an amount of the biologically active substance varying in a predetermined manner along the length of the zone. The biologically active substance can hereby be supplied to the cultivating substance along the said supply zone by different amounts of it being supplied so closely adjacent each other along the areas situated along said zone that the substance is distributed in the cultivating substance substantially as though it has been supplied to the supply zone along a continuous area stretching unbrokenly along the whole length of the supply zone. A holder may be used for supplying the biologically active substance to such neighbouring areas, said holder supporting continuous carriers containing different amounts and/or concentrations of the biologically active substance and which are brought into contact with the cultivated substance for giving off their content of the biologically active substance to it. In this connection the carriers can have the shape, for example, of small porous discs or tubes which are saturated or filled respectively with the biologically active substance. However, for suitably supplying the biologically active substance to the cultivating substance a carrier is suitably used wherein the content of said substance varies along the length of the carrier, the carrier preferably extending over the entire zone of the cultivating substance which is to be supplied with the biologically active substance. Said variation in content can suitably be achieved by using a carrier, the cross-section of area of which varies along the length of the carrier and/or in which concentration in the carrier of the biologically active substance varies along the length of the carrier. The said variation can also be alternatively achieved, possibly in combination with one or both of the aforementioned measures by using a carrier in which porosity varies along its length.

The said carriers can be manufactured from porous material, such as paper or porous plastic, and can be graduated along an elongate side. If the porous carrier material has insufficient liquid absorption ability, this can be improved by incorporating agar therein, for example. It is also possible to allow the carrier to consist of agar or polyakrylamid gel. If the biologically active substance is supplied to the cultivating substance before supplying microorganisms, the carrier can be utilized as an incorporated part of the cultivating substance, or be removed before supplying the microorganisms.

The invention will now be described while referring to the attached drawing.

FIG. 1 is a perspective view of a cultivating apparatus suitable for practising the method according to the invention, and certain parts have been broken away to show the construction of the apparatus more clearly.

FIG. 2 is a view similar to FIG. 1 of a modified cultivating apparatus.

FIG. 3 is a perspective view of another cultivating apparatus.

FIG. 4 shows different types of carrier for biologically active substances.

FIG. 5 is a perspective view to an enlarged scale of a cultivating substance body with a carrier for a biologically active substance applied thereon.

FIG. 6 is a diagram showing examples of concentration gradients which can be obtained by the method according to the invention.

The cultivating apparatus shown in FIG. 1 consists of a vessel 10 with a rectangular bottom and upstanding side walls, and a lid 11. The lid 11 can suitably overlap the side walls of the vessel 10 in the way shown, and be provided with means (not shown) for sealing, for example against the upper edges of the side walls. Inside the vessel 10 a number of separating walls 12–17 project upwardly from its bottom, dividing the vessel into several compartments. In the example shown, said separating walls and the side walls of the vessel form two rows of elongated compartments, side by side, and a row of essentially quadratic compartments situated between these rows. The portions of the walls 12–17, which define the quadratic compartments, are all provided with openings 18 at the bottom of the vessel, neighbouring quadratic compartments communicating with each other through said openings, and through which each quadratic compartment communicates with two of the elongated compartments. The walls 12–17 have less height than the side walls of the vessel 10. The vessel 10 and the lid 11 are suitably made from transparent sterilisable material such as polyacrylate, polycarbonate, polyester plastic or styrene plastic. Ethylene oxide may, for example, be used for sterilization. The elongated compartments can suitably have a length of from 3–15 cm and a width of 0.1–1.2 cm, depending on the type of investigations which are to be carried out. The height of side walls is suitably 0.5–1 cm and that of the separating walls suitably 0.4–0.8 cm.

Cultivating substance, for example of the type described in the introduction, is introduced into the compartments of the vessel 10, and if the supporting substance therein consists of gel, this may be poured into one of the compartments in liquid form and via the openings 18 be allowed to fill all the compartments to desired level, usually to a height of 2–4 mm over the bottom of the vessel.

In FIG. 1 the compartments of the vessel 10 are shown filled with cultivating substance. The lid 11 is furthermore shown provided with pipes 19 or the like, communicating with the interior of the cultivating apparatus, whereby a desired atmosphere can be maintained in the cultivating apparatus by supply and removal of gas through the pipes 19, the ends of which at one end of the lid 11 have been made as connecting studs for this purpose, as is indicated at 20.

The cultivatingg apparatus according to FIG. 2 only differs from the cultivating apparatus according to FIG. 1 in that the vessel 21 has only one separating wall 22 and that the lid 23 does not have means for maintaining a controlled atmosphere in the cultivating apparatus. Together with the side walls of the vessel 21, the separating wall 22 defines two elongated compartments which contain a cultivating substance. At the lower edge of the separating wall 22 an opening 24 is arranged, for reasons explained in connection with FIG. 1.

In FIG. 3 is shown a cultivating device generally of the type which is sold by Orion Diagnostica, Finland, under the name of URICULT ®. It consists of an upwardly open vessel 25 indicated by dotted lines, and a plate 27 attached to a lid 26 for the vessel 25, the plate having a peripheral frame 28 projecting from both sides of the plate. The plate is coated with cultivating substance on both sides, and by means of a rib 29 extending between the end portions of the frame, each side is divided into two separated shallow compartments 30.

When using the cultivating apparatus according to any of FIGS. 1–3, the cultivating substance is inoculated with microorganisms. This can be done, for example by coating the upper side of the cultivating substance in the compartments of the vessel 10 and 21 with liquid samples containing microorganisms, or by dipping the plate 27 in a liquid sample, e.g. a urine sample. Thereafter the cultivating substance in the elongated compartments in the cultivating apparatus according to FIG. 1 and FIG. 3 and the cultivating substance surface in the larger compartment in the cultivating apparatus according to FIG. 2 are supplied with a biologically active substance of the type given in the introduction, along an elongated zone running in the longitudinal direction of the respective compartments. The substance is supplied to these zones in an amount varying in a predetermined way along the length of the zone, suitably while using a carrier of the kind given in the introduction. Such carriers are shown in FIGS. 4 and 5 and are there designated by the numerals 31, 32, 33 and 34 respectively. As has been described above, the biologically active substance will hereby diffuse out into the cultivating substance essentially at right angles in relation to the longitudinal direction of the supply zone, i.e. in a direction towards the bottom of the compartment and the side walls, from the supply zone formed by the contact area between the carrier and the cultivating substance surface. The concentration of the biologically active substance in the cultivatiing substance will then vary along the supply zone and thereby with the longitudinal direction of the compartment in correspondence to the amount of biologically active substance which is supplied to each length section of the supply zone. It is naturally also possible to supply the biologically active substance to the cultivating substance before inoculation. After inoculation and supply of the biologically active substance, the lid 11, 23 and 26 respectively is put on and the sample is cultivated, usually at an increased temperature, whereafter the result is read off by measuring the length of the supply zone along which the growth of the microorganisms has been affected In FIG. 4 are shown examples of carriers for biologically active substances which are taken as being saturated with such a substance, their content of the substance varying along their length due to the face that the cross-sectional area of the carriers varies along their length. The carrier 31 has a constant width, but its height decreases towards one end. Both height and width decrease towards one end for the carrier 32. The carrier 33 has constant width but its height decreases first comparatively quickly and thereafter comparatively slowly towards the one end. The variation in cross-sectional area along the length of the carrier determine the concentration gradient for the cultivating substance put together with the carrier, and it will be appreciated that almost any desired concentration gradient can be obtained in the cultivating substance by a suitable choice of the cross-sectional variation of the carrier along its length.

In FIG. 5 is shown an example of the result which can be obtained by the method according to the invention after cultivating of a microorganism sample. The numeral 35 designates a cultivating substance body, the surface of which was inoculated with microorganisms before cultivation and thereafter to which was applied the carrier 34 for biologically active substance. The concentration of the active substance in the carrier 34, which for example can consist of a strip of porous filter paper, varied in a predetermined way along the length of the carrier, more particularly decreasing from the right to the left hand end of the carrier, as seen in the figure. This variation in concentration was due to the fact that the concentration of the biologically active substance decreased in the carrier from right to left as seen in the figure. To the left in the figure is indicated by dots at 36 the visible occurrence of microorganism colonies grown after cultivation. After the areas denoted by the numeral 37 no such growth occurs however, and therefore, with knowledge of the cross-sectional area of the cultivating substance and the amount of biologically active substance in each length section of the carrier 34, after measuring the length $a$ or $b$ it is easy to calculate the minimum concentration in the cultivating substance which is required to inhibit growth of the microorganisms in question.

Carriers 34 according to FIG. 5, with a concentration of biologically active substance varying along their length can be prepared by their being quickly dipped lengthwise into a standing cylindrical vessel with a removable bottom containing a liquid, including the biologically active substance having a concentration decreasing in a predetermined way, e.g. linearly, from the bottom and upwards, for example. Said gradient in the liquid in the cylindrical vessel can have been achieved by means of a conventional gradient mixer, e.g. of the kind described in Swedish Pat. No. 346,386. Each length section of the carriers will hereby be equilibrated to a concentration of the biologically active substance prevailing at a corresponding level in the vessel. After the necessary equilibrating time, e.g. about 2 hours, the vessel is quickly emptied by removing its bottom, whereafter the carriers are dried in a vacuum. By weighing and measuring the carriers before and after moistening the total amount of the biologically active substance taken up by the carrier can also be determined.

In the diagram according to FIG. 6 are shown the graphs A, B and C of different concentrations which it is desired to obtain in the cultivating substance. In the diagram, the length of the supply zone or the carrier for the biologically active substance is set out along the horizontal axis and along the vertical axis is set out the concentration in percent of the biologically active substance in the cultivating substance, 100% giving the concentration of biologically active substance which is attained with the content in the longitudinal section of the carrier containing the greatest amount of the biologically active substance. The graph denoted by A is suitable when there is interest for a large concentration interval. The graph denoted by B is suitable when there is indeed interest for a large concentration interval, but particular interest for the higher concentrations of the biologically active substance in question within this interval. The graph denoted by C is suitable when there certainly is interest for a large concentration interval, but also particular interest for the lower concentrations of the biologically active substance within the interval.

For the further clarification of the invention some concrete examples of it are described in the following.

EXAMPLE I

A cultivating apparatus, substantially according to FIG. 1, contained in each compartment a 4 mm thick layer of cultivating substance. Each compartment had a length of 50 mm and a width of 8 mm. The cultivating substance constituted a gel, consisting apart from water of 1 % by weight agar and approximately 3 % by weight nutrient of the type sold under the name of BACTO ® by Difco Laboratories, USA. THe cultivating in each compartment was inoculated with microorganisms by having an aqueous suspension of *Escherichia coli*, Strain $K12$, evenly distributed over the area of the cultivating substance. In each compartment excepting one, used solely as a control for the microorganisms really multiplying in the intended manner under the cultivation conditions in question, a carrier or strip of porous filter paper with a length of 50 mm, width 3 mm and a thickenss of 0.5 mm was centrally placed on the surface of the cultivating substance. Each strip contained a total of 0.1 ml antibiotic solution, consisting of penicillin G (manufactured by Kabi AB, Sweden) the amount of antibiotic in each strip increasing constantly from one end of the strip to the other from an amount of 0.002 $\mu$g per mm strip length at one end to 1.1 $\mu$g per mm strip length at the other. The lid of the cultivating apparatus was hereafter put on, and the apparatus was placed upside down in a space wherein a constant temperature of 37° C was maintained. The result was read off after 16 hours, whereat on measuring it was found that the growth rate of the microorganisms in all compartments provided with a strip had been inhibited along a length of 23 ± 1 mm of the cultivating substance surface. As could be easily calculated with guidance from the original amount of penicillin in each part of the strips and the cross-sectional area of the cultivating substance, at least 17 $\mu$g penicillin of the stated type was required per ml cultivating substance to prevent growth of the bacteria in question. This is in good agreement with previously known MIC (minimum inhibitory concentration) data for this bacteria, and shows that the investigation carried out according to the example is extremely reliable.

EXAMPLE II

A cultivating apparatus according to FIG. 1 and Example 1 was charged with cultivating substance according to Example 1. From chromatography paper a number of wedge-shaped carriers were prepared, having a length of 50 mm, a thickness or height of 2mm and a width of 3 mm at one end, decreasing linearly to zero at the other. On testing the strips these were found to be able to absorb 0.15 ml liquid. Five standard solutions of plasma from heparinised human blood and pencillin G (manufactured by Kabi AB, Sweden) were prepared, the standard solutions having a content of 0.5, 1.0, 2.0, 4.0 and 6.0 $\mu$g penicillin per ml respectively. From each one of the standard solutions, 0.15 ml solution was transferred to a wedge-shaped carrier. 0.15 of a plasma sample with an unknown content of penicillin G was transferred to each of a further seven wedge-shaped carriers. The cultivating substance in each compartment of the cultivating apparatus had previously been inoculated with microorganisms by having an aqueous suspension of *Staphylococcus aureus*, strain Oxford, uniformly distributed over the surface of the cultivating substance. The said carriers containing standard solutions and test solutions were placed in the middle of the surface of the cultivating substance in their individual compartments, whereon the lid of the cultivating apparatus was put in place and the cultivating apparatus placed upside down in a space in which a constant temperature of 37° C was maintained. The results were read off after 16 hours by measuring the distances, calculated from the wide end of the wedge-shaped carriers over which the surfaces of the cultivating substance were free from visible bacterial colonies. Starting from the distances obtained from the standard solutions, a standard graph was plotted in a coordinate system. This standard graph was checked mathematically, which was possible since both the original amount and the concentration of penicillin in each part of the carriers containing standard solution and the cross-sectional area of the cultivating substance in each compartment were known. The distances without visible bacteria colonies measured for the unknown sample were found to be 42 + 2 mm, and using the standard graph which has been drawn, it was established that the unknown sample had a content of about 1,1 $\mu$g penicillin per ml test solution.

The invention is not limited to the embodiments described above and illustrated on the drawing, but can naturally be put into practice in many different ways within the scope of the following patent claims.

I claim:

1. A method in examining the effect of a biologically active substance on microorganisms, cultured in the presence of a continuous cultivating substance, the method comprising supplying the biologically active substance to the cultivating substance along an elongated zone in an amount continuously varying in a predetermined manner throughout the length of the zone, said biologically active substance being on a carrier having the ability of giving off to the cultivating substance along said zone an amount of the biologically active substance varying continuously in a predetermined manner throughout along the length of the zone.

2. A method as claimed in claim 1, comprising using a cultvating substance in the form of a body having two defining sides disposed on either side of the elongated zone and substantially parallel to it.

3. A method as claimed in claim 1, comprising using an elongated carrier, whereof the content of the biologically active substance varies continuously along the length of the carrier.

4. A method as claimed in claim 3, comprising using a carrier, the cross-sectional area of which varies continuously along the length of the carrier.

5. A method as claimed in claim 3, comprising using a carrier in which the concentration of the biologically active substance varies continuously along the length of the carrier.

6. A method as claimed in claim 3, comprising using a porous carrier, the porosity of which varies continuously along the length of the carrier.

7. A method according to claim 1, comprising supplying the biologically active substance to the cultivating substance before the supply of microorganisms, and utilizing the carrier as an incorporated part of the cultivating substance.

* * * * *